United States Patent
Chen

(10) Patent No.: US 10,463,281 B2
(45) Date of Patent: Nov. 5, 2019

(54) HEARING TEST METHOD AND SYSTEM, READABLE RECORD MEDIUM AND COMPUTER PROGRAM PRODUCT

(71) Applicant: Invictumtech Inc., Dover, DE (US)

(72) Inventor: Chin-Yang Chen, Taipei (TW)

(73) Assignee: INVICTUMTECH INC., Dover, DE (US)

( * ) Notice: Subject to any disclaimer, the term of this patent is extended or adjusted under 35 U.S.C. 154(b) by 390 days.

(21) Appl. No.: 15/157,489

(22) Filed: May 18, 2016

(65) Prior Publication Data
US 2016/0338622 A1    Nov. 24, 2016

(30) Foreign Application Priority Data
May 22, 2015    (TW) .............................. 104116437 A

(51) Int. Cl.
*A61B 5/12*    (2006.01)
(52) U.S. Cl.
CPC ................ *A61B 5/123* (2013.01); *A61B 5/12* (2013.01); *A61B 5/121* (2013.01)
(58) Field of Classification Search
CPC ............ A61B 5/12; A61B 5/121; A61B 5/123
See application file for complete search history.

(56) References Cited

U.S. PATENT DOCUMENTS

| 8,867,764 B1 * | 10/2014 | Wiggins | A61B 5/121 381/314 |
| 2017/0105079 A1 * | 4/2017 | Koj | A61B 5/123 |
| 2018/0116565 A1 * | 5/2018 | Raz | A61B 5/123 |

FOREIGN PATENT DOCUMENTS

| CN | 102467906 B | 12/2013 |
| TW | 374712 | 11/1999 |
| TW | 441836 | 6/2001 |
| TW | 200708290 | 3/2007 |

OTHER PUBLICATIONS

Guidelines for Manual Pure-Tone Threshold Audiometry; American Speech-Language-Hearing Association.
Acoustics-Loudness Scaling by Means of Categories, ISO 16832, Brand, T; Hohmann, V.
Hearing: an Introduction to Psychological and Physiological Acoustics; Gelfand, S.A., CRC Press; 5 Edition, Dec. 18, 2009.

(Continued)

Primary Examiner — Devin B Henson
(74) Attorney, Agent, or Firm — Muncy, Geissler, Olds & Lowe, P.C.

(57) ABSTRACT

A human hearing test method relates to the following procedures: a musical note from a pre-recorded music in a storage device is loaded by a controller; a next test sound is then selected and played randomly from one of the pre-designed octaves and test frequency bands by using a random number and the musical note loaded by the controller; the sound level of the next test sound is then increasing or decreasing determined by a testing subject's last response to the last test sound and its sound level loaded by the controller from the data recorded earlier in the storage device; a next test sound is determined by the corresponding sound octave number and the musical note loaded by the controller from the storage device, and by the sound level of the test sound.

15 Claims, 5 Drawing Sheets

| Random integer n | Octave y (=n+3) | Note x | | | | | | |
|---|---|---|---|---|---|---|---|---|
| | | C | D | E | F | G | A | B |
| 1 | 4 | C4 | D4 | E4 | F4 | G4 | A4 | B4 |
| | | Frequency band 1 | | | Frequency band 2 | | Frequency band 3 | |
| 2 | 5 | C5 | D5 | E5 | F5 | G5 | A5 | B5 |
| | | Frequency band 4 | | | Frequency band 5 | | Frequency band 6 | |
| 3 | 6 | C6 | D6 | E6 | F6 | G6 | A6 | B6 |
| | | Frequency band 7 | | | Frequency band 8 | | Frequency band 9 | |
| 4 | 7 | C7 | D7 | E7 | F7 | G7 | A7 | B7 |
| | | Frequency band 10 | | | Frequency band 11 | | Frequency band 12 | |

(56) References Cited

OTHER PUBLICATIONS

An Adaptive Procedure for Categorical Loudness Scaling; J. Acoust. Soc. Am., 112(4), pp. 1597-1604.
Loudness, M. Florentine; Popper, A.N.; Fay, R.R.; Springer (2011).
Temporal Integration of Loudness Measured Using Categorical Loudness Scaling and Matching Procedures; Daniel L. Valente, Suyash N. Joshi, Walt Jesteadt; The Journal of the Acoustical Society of America; Jul. 2011; 130(1): EL32-EL37.
English Abstract of CN 102467906B.
English Abstract of Taiwan Search Report.
English Abstract of Taiwanese Examination Report No. 105-04278-10521334640.
English Abstract of TW 200708290.
English Abstract of TW 374712.
English Abstract of TW 441836.
Search Report Taiwan.
Taiwanese Examination Report No. 105-04278-10521334640.

\* cited by examiner

| Random integer n | Octave y (=n+3) | Note x ||||||||
|---|---|---|---|---|---|---|---|---|
| | | C | D | E | F | G | A | B |
| 1 | 4 | C4 | D4 | E4 | F4 | G4 | A4 | B4 |
| | | Frequency band 1 ||| Frequency band 2 || Frequency band 3 ||
| 2 | 5 | C5 | D5 | E5 | F5 | G5 | A5 | B5 |
| | | Frequency band 4 ||| Frequency band 5 || Frequency band 6 ||
| 3 | 6 | C6 | D6 | E6 | F6 | G6 | A6 | B6 |
| | | Frequency band 7 ||| Frequency band 8 || Frequency band 9 ||
| 4 | 7 | C7 | D7 | E7 | F7 | G7 | A7 | B7 |
| | | Frequency band 10 ||| Frequency band 11 || Frequency band 12 ||

FIG. 2

HEARING TEST METHOD AND SYSTEM, READABLE RECORD MEDIUM AND COMPUTER PROGRAM PRODUCT

BACKGROUND

Technical Field

The present invention relates to an electronic device, especially related to a human hearing test method and system.

Related Arts

Human hearing test can be used to provide the objective assessment of the human hearing sensibility. Pure tone audiometry (PTA) is one of the very important hearing tests to date, which provides quantitative assessment to the sound level of the human hearing threshold; categorical loudness scaling offers more perceptual assessment across the entire human hearing range on top of the hearing threshold measurement.

PTA includes a sound familiarization phase and a hearing threshold test phase in general. The sound familiarization phase is to provide demonstrations of the test sound to a testing human subject. The hearing threshold test phase is to test the hearing threshold level of the subject. Test methods and procedures of PTA can be found in American Speech-Language-Hearing Association, (2005). Guidelines for Manual Pure-Tone Threshold Audiometry [Guidelines].

Categorical loudness scaling is to test the hearing range between the maximum and minimum sound levels perceptually, and then to divide the aforementioned hearing range by several pre-designed sub-ranges. Test methods and procedures of the categorical loudness scaling can be found in ISO 16832 "Acoustics-Loudness scaling by means of categories", Brand, T., Hohmann, V., An adaptive procedure for categorical loudness scaling. J. Acoust. Soc. Am., 112(4), pp. 1597-1604 (200) and "Loudness", edited by Florentine M., Popper A. N., and Fay R. R. New York: Springer (2011).

The PTA and categorical loudness scaling methods described above, however, may have inaccurate hearing test results near the hearing threshold (Gelfand S A., 2009. "Hearing: an Introduction to Psychological and Physiological Acoustics", CRC Press; 5 edition, Dec. 18, 2009). Malingering, intending to respond to a predetermined reference level of loudness that is above the real threshold, may cause the false results. Subjects may also perceptually feel the maximum sound level differently at different test frequencies (given the maximum sound levels cannot be provided across all test frequencies). The categorical loudness scaling method may fail to detect such discrepancies from the subjects, and then lead to incorrect hearing assessment in the end; subjects may get tired and boring shortly after PTA test starts.

SUMMARY

To improve the problems stated above, the present invention is to provide a test method and a system, and to use musical notes to replace pure tones to reduce the human response bias during the hearing threshold test, and to obviate potential malingering which leads to false hearing assessment, and to detect different perceptual maximum sound levels from the subject across all test frequencies (provided that the system cannot output maximum sound level at all test frequencies), and to offer more interesting hearing tests to subjects.

The first aspect of the present invention relates to a human hearing test method with the following steps:

loading, by a controller, a musical note from a readable pre-recorded storage device;

generating, by the controller, a random number;

determining, by the controller, an octave number based on the random number, and a test frequency band based on the musical note and the random number for the next test from multiple test frequency bands, wherein each of the test frequency band corresponds to multiple musical notes, and each test frequency band corresponds to each of multiple subject's response data sets;

reading, by the controller, the record of the subject's response and the test sound level of the last test corresponding to the test frequency band in the subject's response data sets from the storage device to derive the increasing or decreasing value of the test sound level for the next test corresponding to the test frequency band; and generating, by the controller, a test sound based on the derived test sound level and the sound data corresponding to the octave number and the musical note, wherein the sound data is loaded from the storage device.

The second aspect of the present invention relates to a human hearing test system including:

a storage device storing music, multiple subject's response data sets, and multiple sound data; and a controller generating a random number, loading a musical note from the storage device, determining an octave number from the random number, determining the test frequency band based on the random number and the musical note for the next test from multiple test frequency bands, wherein each of the test frequency band corresponds to multiple musical notes, and each test frequency band corresponds to each of multiple subject's response data sets, determining the increase or decrease of the next test sound level based on the record of the subject's response and the test sound level of the last test corresponding to the test frequency band in the subject's data sets in the storage device, generating a test sound based on the derived sound level and the sound data corresponding the octave number and the musical note, wherein the sound data is loaded from the storage device.

BRIEF DESCRIPTION OF THE DRAWINGS

FIG. 2 shows the schematic diagram of the test frequency band m, the corresponding octave number y and multiple musical notes x according to the present invention.

WRITTEN DESCRIPTION OF THE PREFERRED EMBODIMENTS

For the purposes of promoting an understanding of the principles of the invention, the hearing test method and system of the present invention are described below, and in applicants' Taiwanese priority application No. 104116437, filed May 22, 2015, the entire contents of which are hereby incorporated herein by reference. The written description and drawings are intended to illustrate the invention in a fashion that allows those who are engaged in the relevant areas are able to understand and appreciate the invention and its preferred embodiments conceptually. It will nevertheless be understood that no limitation of the scope of the invention is thereby intended, with such alterations and modifications to the illustrated device being contemplated as would normally occur to one skilled in the art to which the invention relates.

Figure 1:
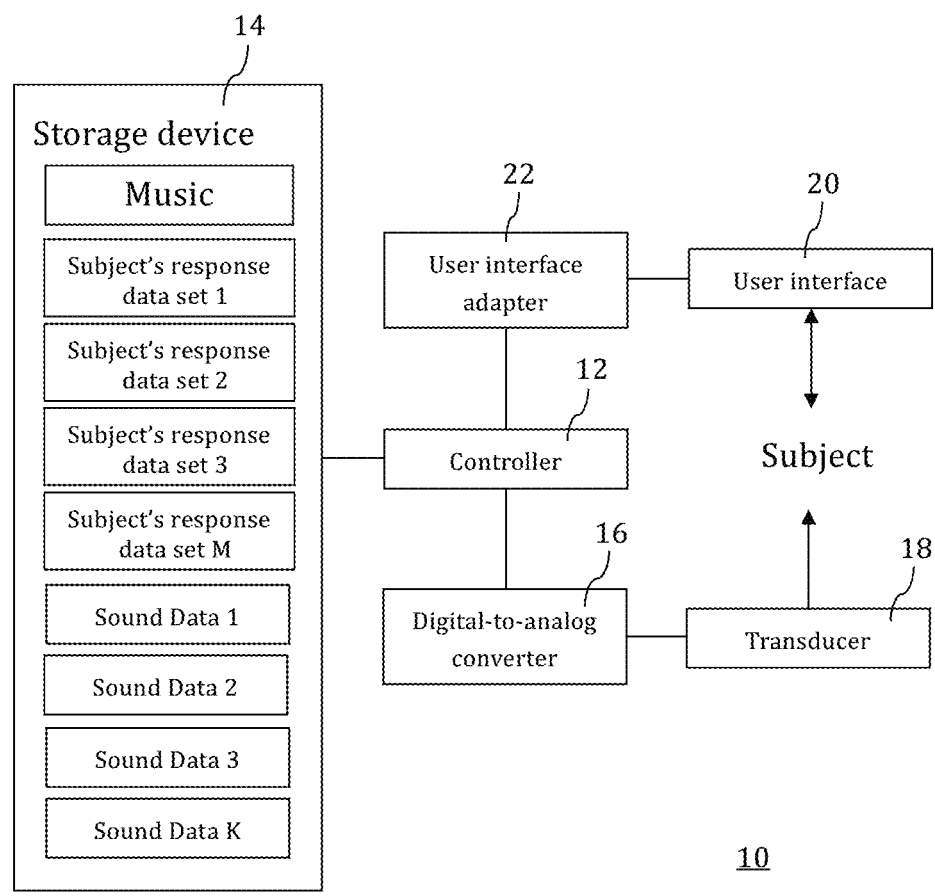
FIG. 1 shows the system block diagram of the human hearing test system according to the present invention.

FIG. 1 indicates the system diagram of the human hearing test system according to the present invention. In FIG. 1, a human hearing test system 10 includes a controller 12, a storage device 14, a digital-to-analog converter 16, a transducer 18, a user interface 20 and a user interface adapter 22. The storage device 14 can be a ROM, a RAM, or a hard disk. The transducer 18 can be an acoustic speaker or a headphone. The user interface can be a touch panel, a computer display, a microphone, a keyboard, or an electronic mouse.

The storage device stores one or more music, multiple subject's response data sets 1, 2, . . . , M and multiple sound data 1, 2, . . . , K. The music is composed of multiple musical notes x. Each of the test frequency bands 1, 2, . . . , M corresponds to each of the multiple subjects' response data sets 1, 2, . . . , M. A subject's response data set m includes the subject's responses to the multiple tests corresponding to the test frequency band m, the associated test result and the test sound levels, that is, the subject's response data set 1 includes the subject's responses to the multiple tests corresponding to the test frequency band 1, the associated test results and the test sound levels, while the subject's response data set 2 includes the subject's responses to the multiple tests corresponding to the test frequency band 2, the associated test tests and the sound levels, and so on. The multiple sound data 1, 2, . . . , K are created in the form of the note-octave pitch notation based on an octave number y and a musical note x.

In the present embodiment, the controller 12 generates a number n randomly between 1 and 4. In this embodiment, an integer generated randomly between 1 and 4 is an example, but not limited to the application of the present invention.

The feature of the present invention is illustrated as follows: The controller 12 obtains the octave number y by the random number n based on the equation: octave number y=random number n+3. The musical note x is then loaded by the controller from the music in the storage device 14, and the test frequency band m is then determined by the random number n and the multiple musical notes x within an octave number y. As shown in FIG. 2, the test frequency band m is determined by the following equations:

test frequency band m=1+3*(random number n−1), if the pitch of the musical note x belongs to the pitch class C, D, or E;

test frequency band m=2+3*(random number n−1), if the pitch of the musical note x belongs to the pitch class F, or G;

test frequency band m=3+3*(random number n−1), if the pitch of the musical note x belongs to the pitch class A or B;

The controller 12 uses a pre-determined value as an initial test sound level at the beginning of the hearing test, or reads the record of the subject's response from the subject's response data set m corresponding to the test frequency band m and its associated test result and the test sound level to derive the increasing or decreasing value of the test sound level in the next test at the test frequency band m.

The controller 12 reads the pre-recorded sound data of musical sound (such as sounds of musical instruments, mono tones, narrowband test signal, warble tone, and so on) with the corresponding octave number y and musical note x from the storage device 14 to create a test sound. Each of the sound data corresponds to one test frequency band at least. In the alternative embodiment, the sound data can be generated by a software synthesizer run by the controller 12.

In this embodiment, the musical sounds are presented by the flute and the piano. The illustration is provided for the explanation, and is not used to limit the present invention. Any musical sound is applicable to the present invention. 12 frequency bands are used as an example, shown in FIG. 2, in the present invention, and the quantity and the position of the test frequency bands can be determined also by the musical note's position.

The digital-to-analog converter 16 receives the digital test sound signal transmitted from the controller 12, and then converts this digital test sound signal to the analog test sound signal. The transducer 18 then receives the analog test sound signal transmitted from the digital-to-analog converter 16, and converts the analog test sound signal to the acoustic test signal for the subject's hearing test.

Figure 3:
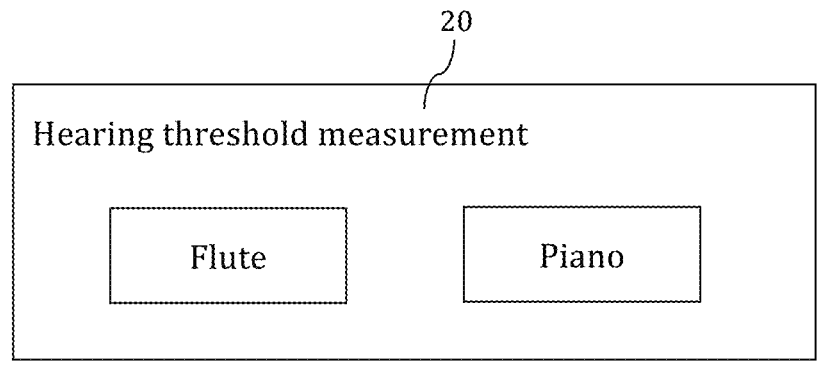
FIG. 3 shows the schematic diagram of displaying the choice of the musical instruments at the user interface according to the present invention.
Figure 4:
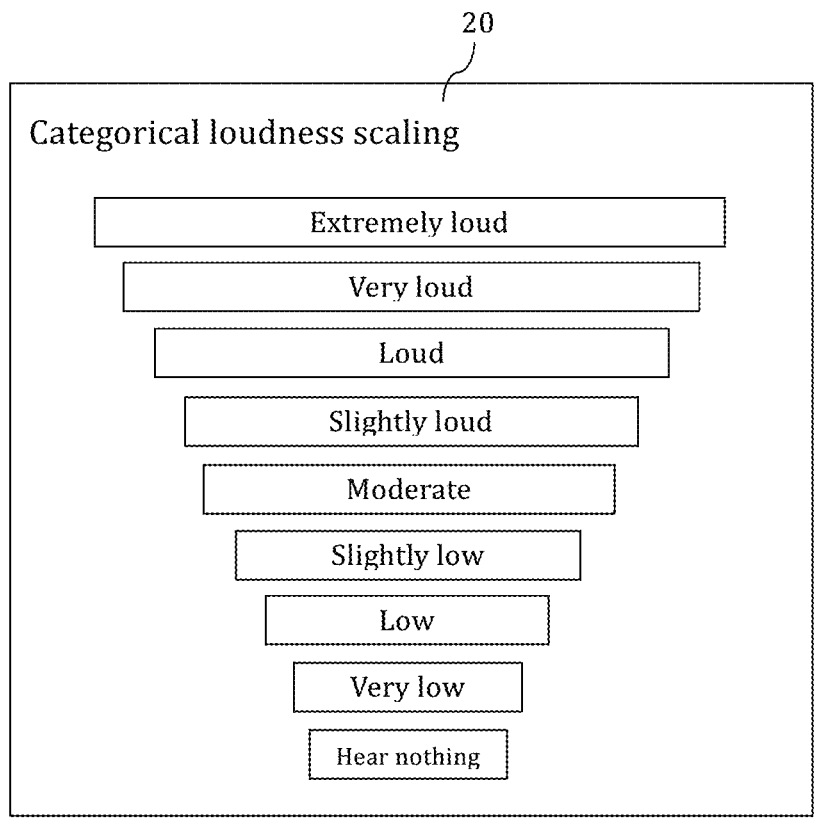
FIG. 4 shows the schematic diagram of displaying the loudness options at the user interface according to the present invention.

FIG. 3 is a schematic diagram to demonstrate the choices of the musical instruments at the user interface. FIG. 4 is a schematic diagram to display the loudness options at the user interface. The subject in the hearing test responds to the test sound corresponding to the test frequency band m at the user interface 20 in FIG. 3 or FIG. 4 by choosing the musical instruments or loudness options, or does not respond to the test sound. The user interface 20 sends the subject's test response to the controller 12 with the help of the user interface adapter 22. The controller 12 then compares the subject's response (or no response) with the known data to conclude if the subject can hear the test sound correctly, and saves the subject's response, test results and the sound level of the current test into the subject's response data set m corresponding to test frequency band m in the storage device 14.

During the sound familiarization phase, the controller 12 starts the hearing test by presenting the musical sound with an initial test sound level (say 30 dB) in the corresponding test frequency band m. If the subject has a wrong response or no response, the controller 12 will save the test sound level of the current test into the subject's response data set m corresponding to the test frequency band m in the storage device 14 as the reference to the test sound level of the next test. The test sound level will be increased by a constant (say 10 dB) in the next test corresponding to the test frequency band m. On the other hand, if the subject has the correct response, which means choosing the correct musical instruments at the user interface 20 (shown in FIG. 3), the test sound level will be decreased by a constant (say 10 dB) as an initial test sound level for the next hearing threshold test phase corresponding to the test frequency band m.

During the hearing threshold test phase, the controller starts the hearing test by employing the test sound level acquired in the sound familiarization phase as the initial test sound level in the corresponding test frequency band m. If the subject has wrong response or no response, the controller 12 will save the current sound level of the test sound into the subject's response data set m corresponding to the test frequency band m in the storage device 14. The test sound level will then be increased by a first constant (say 5 dB) as the new sound level of the test sound in the next test corresponding to the test frequency band m.

If the subject has the correct response, which means choosing the correct musical instruments at the user interface 20 (shown in FIG. 3), the controller 12 will save the current sound level of the test sound into the subject's response data set m corresponding to the test frequency band m in the storage device 14. The test sound level will then be decreased by a second constant (say 10 dB) as the new sound level of the test sound in the next test corresponding to the test frequency band m.

The controller will assign the test sound level to the hearing threshold corresponding to the test frequency band m if it finds at least half of the last N-round tests corresponding to the test frequency band m have the same sound level to be decreased by the second constant. The same procedure is repeated for other test frequency bands till the subject's hearing thresholds corresponding all of the test frequency bands are all measured. The controller 12 then ends the human hearing threshold test.

During the categorical loudness scaling test, the controller 12, as mentioned in the Related Arts, combines the musical notes with the octave number to generate the test sounds corresponding to the test frequency band m with an initial test sound level (say 65 dB) for the subject's testing. The increments and decrements in the sound levels of the test sounds corresponding to the test frequency band m can be adjusted. The test sounds with the increments in sound levels are then played alternatively with the test sounds with the decrements in sound levels as the test goes on till the perceptual "extremely loud" option at the user interface 20 is rated by the subject and the perceptual "very soft" option at the user interface 20 is rated by the subject, respectively.

The hearing range, corresponding to the test frequency band m, between the perceptual "extremely loud" and "very soft" option is partitioned to several sub-ranges, and the sound levels of the test sounds, created by the controller 12 according to the musical note and the octave number, are generated to map to those sub-ranges correspondingly.

In another embodiment of the categorical loudness scaling test, the reference sound corresponding to the test frequency band m is generated by the controller 12 based on the sound level of the last test sound and the sound level of the next test sound corresponding to the test frequency band m. The sound level of the reference sound, for instance, is the average of the sound level of the last test sound and the current test sound.

The subject is not required to respond to the reference sound generated by the controller 12. The next test sound corresponding to the test frequency band m is then created and played by the controller 12 after the reference sound. The subject will rate the option of the loudness according to the sound level of the next test sound. Applying the reference sound is to reduce the response bias due to the significant difference between the sound levels of two consecutive test sounds (say perceptually "extremely loud" and "very soft" sounds played consecutively).

Figure 5:
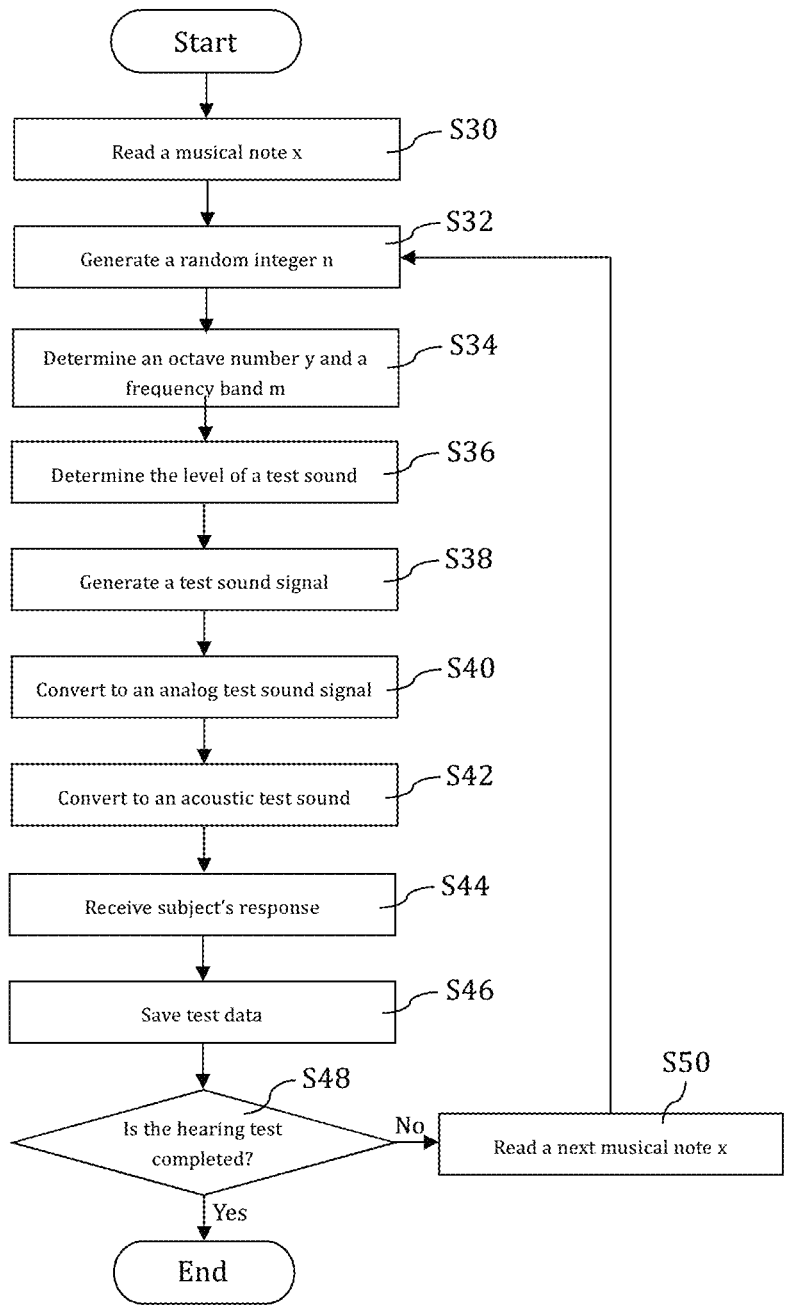
FIG. 5 shows the flow chart of the human hearing test method according to the present invention.

FIG. 5 shows the flow chart of the hearing test method revealed in the present invention. FIG. 1 to FIG. 4 will be referred to explain the procedures shown in FIG. 5.

In FIG. 5, the first musical note x (Step S30) is loaded from the storage device 14 by the controller 12. A random integer n, between 1 and 4, is then generated by the controller 12 (Step S32).

The octave number y is determined by the random number n: octave number y=random number n+3, generated from the controller 12. The test frequency band m is then determined by the octave number y and the first musical note x (Step S34), as explained earlier.

The first test sound is created from the test frequency band m with an initial sound level pre-assigned by the controller 12. The rest of the test sound levels corresponding to the test frequency band m will be determined by the subject response data set m saved in the storage device 14, which includes the subject's responses (the controller 12 will calculate the correctness of the subject response), the associated test result (the user interface 20 has received the subject input or not), and the sound levels of the test sounds. The next test sound level corresponding to the test frequency band m is then increased or decreased according to the subject's last response (or no response) corresponding to the test frequency band m (Step S36).

At Step S36, during the sound familiarization phase mentioned in the Related Arts, the controller 12 starts the hearing test corresponding to the test frequency band m with an initial test sound level (say 30 dB). If the subject has an incorrect response or no response, the controller 12 will save the current test sound level into the subject's response data set m in the storage device 14. The controller 12 will increase the sound level of the next test sound corresponding to the test frequency band m by a constant (say 10 dB)

If the subject has the correct response, which means the subject can hear the test sound corresponding to the test frequency band m originally created from the musical note and choose the correct musical instrument at the user interface 20 (shown in FIG. 3), the current sound level of the test sound will be saved as the initial test sound level for the next hearing threshold test phase corresponding to the test frequency band m.

During the hearing threshold test phase, the controller 12 starts the test corresponding to the test frequency band m by using the initial test sound level acquired at the sound familiarization phase. If the subject has an incorrect response or no response, the controller 12 will save the current sound level of the test sound into the subject's response data set m in the storage device 14, and increase the current sound level by a first constant (say 5 dB) as the sound level of the next test sound corresponding to the test frequency band m.

If the subject has the correct response, which means the subject can hear the test sound corresponding to the test frequency band m originally created from the musical note and choose the correct musical instrument at the user interface 20 (shown in FIG. 3), the controller 12 will save the current sound level of the test sound into the subject's response data set m in the storage device 14, and decrease the current sound level by the second constant (say 10 dB) as the sound level of the next test sound corresponding to the test frequency band m.

During the categorical loudness scaling test, the controller 12 mentioned in the Related Arts starts the test corresponding to the test frequency band m with an initial sound level of the test sound (say 65 dB). The increments or decrements in the sound levels of the test sounds corresponding to the test frequency band m can be adjusted. The test sounds are then played in the alternative order, that is, the test sounds with the increments in sound levels will be followed by test sounds with the decrements in sound levels, and vice versa. The "extreme loud" option is rated by the subject at the user interface 20 (shown in FIG. 4) indicates the perceptual loudness of the test sound corresponding to the test frequency band m heard by the subject is extremely loud and uncomfortable, while the "very soft" option rated by the subject at the user interface 20 (shown in FIG. 4) reflects the perceptual loudness of the test signal corresponding to the test frequency band m heard by the subject is near silent and just barely heard. The controller 12, according to FIG. 4, partitions the hearing range between "extreme loud" and "very soft" into sub-ranges which are, for example, equally spanned in the loudness scale to test the hearing perception of the subject corresponding to the test frequency band m.

The test sound, such as the sound of the flute or piano on the FIG. 3 corresponding to the test frequency m, can be created by the controller 12 based on a sound data, corresponding to the octave number y and the musical note x, loaded from the storage device 14, or the test sound can be created by a software synthesizer run by the controller 12 according to the octave number y and the musical note x (Step S38), wherein the sound level of the test sound is determined by the Step S36.

The digital-to-analog converter 16 receives the digital test sound signal transmitted from the controller 12, and converts the digital test sound signal to the analog test sound signal (Step S40).

The transducer 18 receives the analog test sound signal from the digital-to-analog converter 16, and converts the analog test sound signal to the acoustical test sound originally created from the musical note and the octave number with the sound level determined in S36 for the subject's testing (Step S42).

The subject responds to the test sound corresponding to the test frequency band m at the user interface 20 shown in FIGS. 3 and 4. For example, the subject can choose the flute or the piano or not choose the options at the user interface 20 shown in FIG. 3 during the hearing threshold test, or choose the perceptual loudness rating at the user interface 20 shown in the FIG. 4 during the categorical loudness scaling test. The test result corresponding to the test frequency band m is then feedback from the user interface 20 and sent to the controller 12 through the user interface adapter 22 (Step S44).

The controller 12 saves the correctness of the subject's response, the associated test result, and the current sound level of the test sound, corresponding to the test frequency band m into the subject's response data set m in the storage device 14 (Step S46).

In the present embodiment, the combination of the musical note, the octave number, and the correct musical instrument chosen at the user interface 20 can obviate potential malingering which needs consistent responses to a randomized sequence of test sounds.

The controller 12 ends the hearing test based on Step 48. During the hearing threshold test, for example, the controller 12 checks the test sound levels of the last N rounds corresponding to the test frequency band m, and will conclude the hearing threshold is obtained if at least half of the last N-round tests have the same decreased second constant sound level of the test sounds. The controller 12 will end the hearing threshold test if the subject's hearing threshold is recorded for each of the test frequency band m, or end the categorical loudness scaling test if the number of the test iterations is equal to the pre-designed value corresponding to the test frequency band m.

If the hearing test is not completed, the controller loads the next musical note x from the storage device 14 (Step S50), and proceeds to Step S32.

Figure 6:
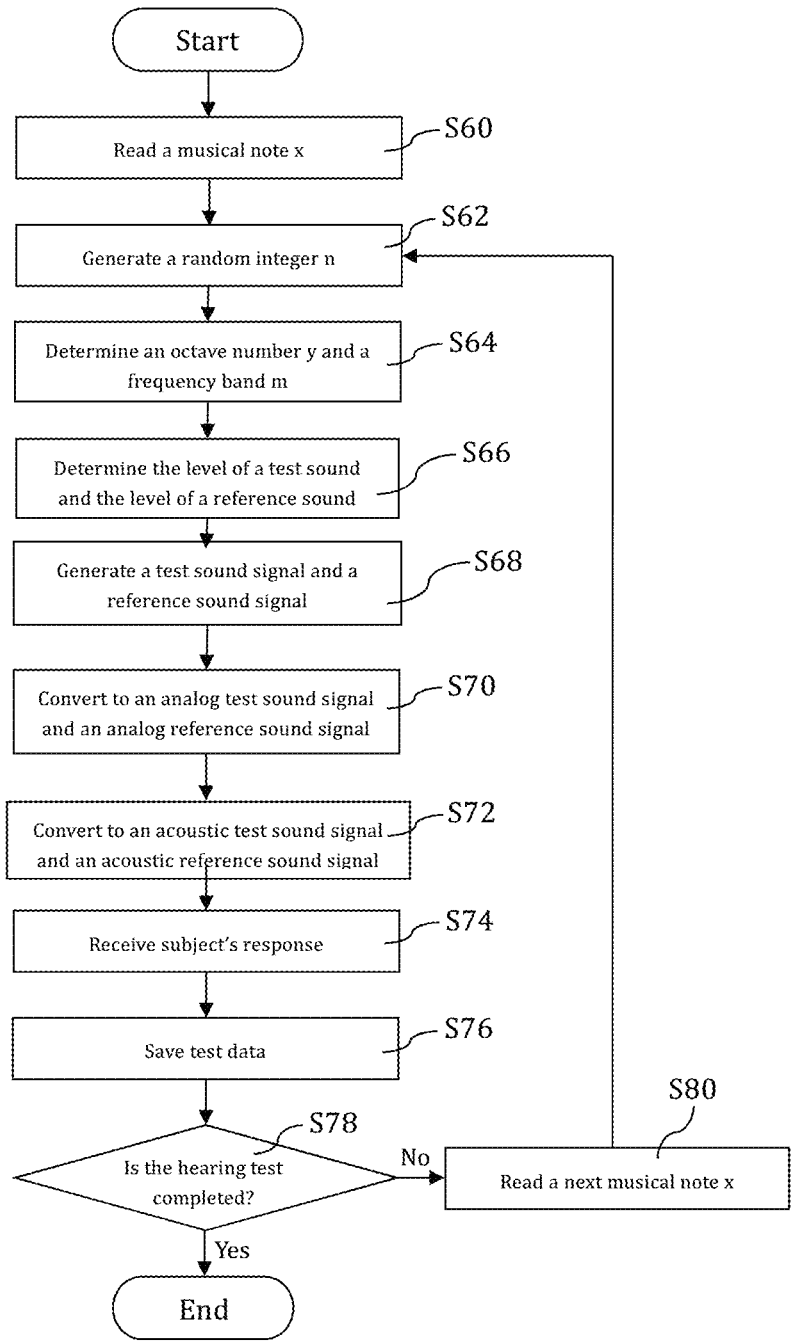
FIG. 6 shows the flow chart of the human hearing test method according to another embodiment of the present invention.

FIG. 6 illustrates the flow chart of another embodiment of the present invention. FIGS. 1 to 4 are referred for explaining the procedures demonstrated in FIG. 6.

Step S60, S62, S64 in FIG. 6, and Step S30, S32, S34 in FIG. 5 share the same operations, so the explanation corresponding to Step S60, S62, S64 in FIG. 6 is omitted herein.

The controller 12 starts the hearing test at the test sound corresponding to the test frequency band m with an initial sound level, or otherwise uses the record of the subject's response, the associated test result, and the test sound level of the last test in the subject's response data set m corresponding to the test frequency band m to determine the current test sound level. The procedures in the sound familiarization phase of the hearing threshold test, the procedures in the hearing threshold test phase of the hearing test, and the procedures in the categorical loudness scaling test are the same as the procedures in Step S36 (FIG. 5), so the description of these procedures are omitted herein.

The controller 12 generates the current test sound corresponding to the test frequency band m based on the subject's response data set m, including the subject's response, the associated test result, and test sound level, and creates a reference sound corresponding to the test frequency band m with the sound level between the last and the current sound level of the test sounds. The sound level of the reference sound, for instance, is the average of the sound level of the last test sound and the sound level of the current test sound (Step S66).

The reference sound and the test sound, such as the sound of the flute or piano in FIG. 3 corresponding to the test frequency m, can be created based on the sound data corresponding to the musical note x and the octave number y loaded from the storage device 14, or can be created by a software synthesizer run by the controller 12 according to the octave number y and the musical note x (Step S68), wherein the sound levels of the test sound and the reference sound corresponding to the test frequency band m are obtained according to Step S66.

The digital-to-analog converter 16 receives the digital test sound and reference sound signals transmitted from the controller 12, and converts to the analog test sound and reference sound signals (Step S70).

The transducer 18 receives the analog test sound and reference sound signals from the digital-to-analog converter 16, and converts to the acoustic test sound and reference sound for the hearing test (Step S72).

The subject does not need to respond to the reference sound played at first, but need to respond to the subsequent test sound by choosing the flute, the piano, or not choosing any option displayed at the user interface 20 shown in FIG. 3 or 4. The subject can choose the flute or the piano or not respond at the user interface 20 shown in FIG. 3 during the hearing threshold test. The subject can also rate the perceptual loudness options displayed at the user interface 20, shown in FIG. 4, during the categorical loudness scaling test. The test result corresponding to the test frequency band m is sent to the controller 12 through the user interface adapter 22 (Step S74).

Step S76, S78, S80 in FIG. 6, and Step S46, S48, S50 in FIG. 5 share the same procedures, so the details corresponding to Step S76, S78, S80 in FIG. 6 are omitted herein.

The present invention is to provide a human hearing test method and system which replaces the pure tones with musical sounds, reduces possible test inaccuracy in the hearing threshold test, and obviates potential malingering. The present invention is also to examine the possibly different perceptual maximum loudness across different test frequency bands (provided that the system cannot output the maximum loudness at certain frequency bands) during the categorical loudness scaling test. Finally, the present invention is more appealing to the subject of the hearing test.

Although the present invention has been stated as above with reference to the preferred embodiments and exemplary drawings, the preferred embodiments and exemplary drawings should not be regarded as limitations. Various modifications, omissions and variations made to the forms and contents of the embodiments by the person skilled in the art do not depart from the scope claimed by the claims of the present invention. Additionally, any or all of the features, elements, and/or embodiments disclosed herein may be combined with any or all of the other features, elements, and/or embodiments disclosed herein to provide a system or method that comprises or consists essentially of such features, elements, and/or embodiments.

What is claimed is:

1. A hearing test method, comprising the steps of:
   reading, by a controller, a musical note from a storage device;
   generating, by the controller, a random number having a numerical value;
   determining, by the controller, an octave number by adding the random number to a predetermined numerical value, and a frequency band, based on the musical note and the random number, for a next test from multiple test frequency bands, wherein each of the test frequency bands corresponds to multiple musical notes, and each test frequency band corresponds to each of multiple subject's response data sets;
   reading, by the controller, a record of a subject's response and a test sound level of a last test corresponding to the test frequency band in the subject's response data sets from the storage device to derive an increasing or decreasing value of the test sound level for the next test corresponding to the test frequency band; and
   generating, by the controller, a test sound signal based on a derived test sound level and the sound data corresponding to the octave number and the musical note, wherein the sound data is loaded from the storage device or the sound data is generated by the controller.

2. The hearing test method according to claim 1, wherein the sound data comprise musical sounds, and each of the musical sounds corresponds to at least one of the test frequency bands.

3. The hearing test method according to claim 1, further comprising the steps of:
   receiving, by a digital-to-analog converter, the test sound signal which is a digital test sound signal transmitted by the controller, and converting the digital test sound signal to an analog test sound signal;
   receiving, by a transducer, the analog test sound signal transmitted by the digital-to-analog converter, and converting the analog test sound signal to an acoustic test signal for the subject's hearing testing;
   receiving, by a user interface, the subject's response to the hearing test and generating, by a user interface, a test result based on the subject's response;
   receiving, by the controller, the test result transmitted by the user interface, generating a test response data based on judgment on the test result, and then saving the test response data, the associated test result and the sound level of the test sound signal into the subject's response data set corresponding to the test frequency band in the storage device;
   determining, by the controller, whether the hearing test should end or not; and
   reading, by the controller, a next musical note from the storage device and proceeding to the step of generating a random number.

4. The hearing test method according to claim 3, further comprising:
   determining, by the controller, to increase or decrease the sound level of the test sound signal corresponding to the test frequency band to be tested in the next test during a sound familiarization phase and a hearing threshold test phase of the hearing test,
   wherein the sound familiarization phase includes the following steps s:
      starting, by the controller, a sound familiarization phase by presenting a sound with an initial sound level;
      saving, by the controller, the sound level of a current test sound signal into a subject's response data set corresponding to the test frequency band in the storage device, and increasing the sound level of the test sound for the next test at the test frequency band by a constant if the subject has no response or does not respond correctly to the test sound; and
      setting, by the controller, an initial sound level for a next hearing threshold test phase corresponding to the test frequency band based on the sound level of the current test sound if the subject responds correctly to the current test sound; and
   wherein the hearing threshold test phase includes the following steps:
      starting, by the controller, the hearing threshold test phase by presenting a test sound signal with the initial sound level for the hearing threshold test phase;
      saving, by the controller, the sound level of the current test sound signal into a subject's response data set corresponding to the test frequency band in the storage device, and increasing the sound level of the test sound for the next test at the test frequency band by a first constant if the subject has no response or does not respond correctly to the test sound;
      saving, by the controller, the sound level of the current test sound signal into a subject's response data set corresponding to the test frequency band in the storage device, and decreasing the sound level of the test sound for the next test at the test frequency band by a second constant if the subject respond correctly to the test sound;
      evaluating, by the controller, the test sound levels of last N-round tests corresponding to the test frequency band continuously, where N is a predetermined integer corresponding to the test frequency band, till at least half of the N-round tests corresponding to the test frequency band have a same sound level to be decreased by the second constant; and
      assigning, by the controller, the test sound level for the next test to the hearing threshold corresponding to the test frequency band; and the step of determining, by the controller, when to end the hearing test comprises: checking, by the controller, if the subject's hearing thresholds corresponding all of the test frequency bands are all measured.

5. The hearing test method according to claim 3, and further comprising the steps of:
   generating, by the controller, a reference sound signal;
   receiving, by the digital-to-analog converter, the reference sound signal which is a digital signal transmitted by the controller, and converting the reference sound signal to a second analog sound signal; and
   receiving, by the transducer, the second analog sound signal transmitted by the digital-to-analog converter, and converting the second analog sound signal to a second acoustic signal.

6. The hearing test method according to claim 5, further comprising:

presenting, by the controller, test sound signals with two alternating sound level sequences which start at an initial sound level and adjust the increments or decrements in an other sound levels, and obtaining the sound level of a "very soft" sound when option "very soft" is rated by the subject, and obtaining the sound level of an "extremely loud" sound when option "extremely loud" is rated by the subject;

partitioning, by the controller, a hearing range between "extreme loud" and "very soft" into multiple sub-ranges in a loudness scale, and generating multiple test sound signals corresponding to the sub-ranges; and determining, by the controller, a sound level for a reference sound, wherein the sound level for the reference sound is between the sound level of the last test sound and the sound level of the current test sound.

7. A hearing test system, comprising:
a storage device that stores music, multiple subject's response data sets and multiple sound data; and
a controller generating a random number having a numerical value, loading a musical note from the storage device, determining an octave number by adding the random number to a predetermined numerical value, determining the test frequency band based on the random number and the musical note for a next test from multiple test frequency bands, wherein each of the test frequency bands corresponds to multiple musical notes, and each test frequency band corresponds to each of multiple subject's response data sets, determining increase or decrease of a next test sound level based on a record of a subject's response and a test sound level of a last test corresponding to the test frequency band in the subject's data sets in the storage device, and generating a test sound signal based on a derived sound level and the sound data corresponding the octave number and the musical note, wherein the sound data is loaded from the storage device or the sound data is generated by the controller.

8. The hearing test system according to claim 7, wherein the sound data comprise musical sounds, and each of the musical sounds corresponds to at least one of the test frequency bands.

9. The hearing test system according to claim 7, further comprising:
a digital-to-analog converter that receives the test sound signal which is a digital test sound signal transmitted by the controller, and converting the digital test sound signal to an analog test sound signal;
a transducer that receives the analog test sound signal transmitted by the digital-to-analog converter, and converting the analog test sound signal to an acoustic test signal for the subject's hearing testing; and
a user interface receiving the subject's response to the hearing test, generating a test result based on the subject's response, and sending the test result to the controller via a user interface adapter;
wherein the controller generates a test response data based on judgment on the test result, saves the test response data, the associated test result and the sound level of the test sound signal into the subject's response data set corresponding to the test frequency band in the storage device, and determines when to end the hearing test.

10. The hearing test system according to claim 9, wherein the user interface is a touch panel, a screen, a microphone, a keyboard or a mouse.

11. The hearing test system according to claim 9, wherein the transducer is a loudspeaker or an earphone.

12. The hearing test system according to claim 9, wherein the controller determines to increase or decrease the sound level corresponding to the test frequency band to be tested in the next test during a sound familiarization phase and a hearing threshold test phase of the hearing test,
the sound familiarization phase includes the following steps:
starting the sound familiarization phase by presenting a sound with an initial sound level;
saving the sound level of a current test sound signal into a subject's response data set corresponding to the test frequency band in the storage device, and increasing the sound level of the test sound for the next test at the test frequency band by a constant if the subject has no response or does not respond correctly to the test sound; and
setting an initial sound level for a next hearing threshold test phase corresponding to the test frequency band based on the sound level of the current test sound if the subject responds correctly to the current test sound; and
the hearing threshold test phase includes the following steps:
starting the hearing threshold test phase by presenting a test sound signal with the initial sound level for the hearing threshold test phase;
saving the sound level of the current test sound signal into a subject's response data set corresponding to the test frequency band in the storage device, and increasing the sound level of the test sound for the next test at the test frequency band by a first constant if the subject has no response or does not respond correctly to the test sound;
saving the sound level of the current test sound signal into a subject's response data set corresponding to the test frequency band in the storage device, and decreasing the sound level of the test sound for the next test at the test frequency band by a second constant if the subject respond correctly to the test sound;
evaluating the test sound levels of last N-round tests corresponding to the test frequency band continuously, where N is a predetermined integer greater corresponding to the test frequency band, till at least half of the N-round tests corresponding to the test frequency band have a same sound level to be decreased by the second constant;
assigning the test sound level for the next test to the hearing threshold corresponding to the test frequency band; and
ending the hearing test by checking if the subject's hearing thresholds corresponding all of the test frequency bands are all measured.

13. The hearing test method according to claim 9, wherein:
the digital-to-analog converter receives the reference sound signal which is a second digital signal transmitted by the controller, and converts the reference sound signal to a second analog sound signal; and
the transducer receives the second analog sound signal transmitted by the digital-to-analog converter, and converts the signal analog sound signal to a second acoustic signal.

14. The hearing test system according to claim 13, wherein the controller determines to increase or decrease the sound level for the next test by executing the following steps:

presenting test sound signals with two alternating sound level sequences which start at an initial sound level and adjust the increments or decrements in an other sound levels, and obtaining the sound level of a "very soft" sound when option "very soft" is rated by the subject, and obtaining the sound level of an "extremely loud" sound when option "extremely loud" is rated by the subject;

partitioning a hearing range between "extreme loud" and "very soft" into multiple sub-ranges in a loudness scale, and generating multiple test sound signals corresponding to the sub-ranges; and determining, by the controller, a sound level for a reference sound, wherein the sound level for the reference sound is between the sound level of the last test sound and the sound level of the current test sound.

15. The hearing test system according to claim 7, wherein the storage device is a ROM, a RAM or a hard disc.

* * * * *